United States Patent
Batsukh et al.

(10) Patent No.: US 11,583,664 B2
(45) Date of Patent: Feb. 21, 2023

(54) BALLOON CATHETER ASSEMBLY FOR INSERTION AND POSITIONING THERAPEUTIC DEVICES WITHIN A VASCULAR SYSTEM

(71) Applicants: STRYKER CORPORATION, Kalamazoo, MI (US); STRYKER EUROPEAN OPERATIONS LIMITED, Carrigtwohill (IE)

(72) Inventors: Enkhsanaa Batsukh, Kalamazoo, MI (US); Huey Chan, San Jose, CA (US)

(73) Assignees: Stryker Corporation, Kalamazoo, MI (US); Stryker European Operations Limited, Carrigtwohill (IE)

( * ) Notice: Subject to any disclaimer, the term of this patent is extended or adjusted under 35 U.S.C. 154(b) by 600 days.

(21) Appl. No.: 16/677,505

(22) Filed: Nov. 7, 2019

(65) Prior Publication Data
US 2021/0138210 A1   May 13, 2021

(51) Int. Cl.
*A61M 25/10*   (2013.01)

(52) U.S. Cl.
CPC . *A61M 25/1027* (2013.01); *A61M 2025/1077* (2013.01); *A61M 2025/1079* (2013.01)

(58) Field of Classification Search
CPC ...... A61M 25/1027; A61M 2025/1077; A61M 2025/1079; A61B 2017/22001; A61B 2017/22002
See application file for complete search history.

(56) References Cited

U.S. PATENT DOCUMENTS

| | | | | |
|---|---|---|---|---|
| 5,176,698 A | * | 1/1993 | Burns | A61M 25/104 606/192 |
| 6,638,245 B2 | | 10/2003 | Miller et al. | |
| 2014/0188043 A1 | | 7/2014 | Shibahara | |
| 2020/0352550 A1 | * | 11/2020 | Maeda | A61M 25/1002 |

FOREIGN PATENT DOCUMENTS

| | | |
|---|---|---|
| EP | 0277369 | 8/1988 |
| WO | 92/11894 | 7/1992 |
| WO | WO 92/11894 | 7/1992 |

OTHER PUBLICATIONS

PCT International Search Report and Written Opinion for International Appln. No. PCT/US2020/058986, Applicant Stryker Corporation, dated Apr. 28, 2021 (17 pages).

PCT Invitation to Pay Additional Fees for International Patent Appln. No. PCT/US2020/058986, Applicant Stryker Corporation, dated Mar. 3, 2021 (15 pages).

* cited by examiner

*Primary Examiner* — Kathleen S Holwerda
(74) *Attorney, Agent, or Firm* — Vista IP Law Group, LLP

(57) ABSTRACT

A balloon catheter which allows for faster preparation and effective purging of air. The balloon catheter includes an elongated, flexible catheter having an inner lumen. A balloon member is secured to an outer surface of a distal portion of the catheter such that an inner surface of the balloon member and an outer surface of the catheter define an inflatable balloon interior. The catheter has an inflation lumen connected to an inflation port and extending distally to a distal end in fluid communication with the inflatable balloon interior. One or more purge apertures are provided in a wall of the catheter, each forming a fluid path between the (Continued)

inflatable balloon interior and the inner lumen of the catheter to allow for purging air from the catheter prior to use in a medical procedure.

24 Claims, 21 Drawing Sheets

BALLOON CATHETER ASSEMBLY FOR INSERTION AND POSITIONING THERAPEUTIC DEVICES WITHIN A VASCULAR SYSTEM

FIELD OF THE INVENTION

The disclosed inventions generally relate to medical devices and methods for performing procedures within a lumen of a vascular system of a patient, and more particularly, to devices and methods for preparing a balloon catheter for insertion within a vascular system by purging unwanted air bubbles from the balloon inflation lumen and balloon interior.

BACKGROUND

Various designs of medical catheters have been previously provided for performing a variety of medical procedures, including interventional therapy, drug delivery, diagnosis, perfusion, and the like. In general, medical catheters are used by introducing the catheter through an entry site of a patient and into the vascular system of the patient, such as a vein or artery. The catheter is advanced from the entry site by guiding and pushing the catheter through the vascular system to a target site for performing a therapeutic and/or diagnostic medical procedure.

An example of one type of intravascular catheter is a balloon catheter which includes an elongated tubular member, wherein a balloon member is affixed, for example, to a distal end portion of the tubular member or other suitable location to form an inflatable balloon interior between an inner surface of the balloon member and the outer surface of the tubular member. The tubular member includes an inflation lumen extending from a proximal end of the tubular member to the inflatable balloon interior for injecting fluid—to thereby inflate—the balloon. Various types of balloon catheters have been previously disclosed for performing a variety of different medical procedures. For instance, balloon catheters for diagnosing and treating neurological disorders, such as ischemic stroke, are disclosed in U.S. Pat. No. 6,638,245 (the '245 patent), the disclosure of which is fully incorporated herein. FIGS. 13A and 13B illustrate a prior art balloon catheter 150 as disclosed in the '245 patent. The balloon catheter 150 comprises an outer tubular member 170 and an inner tubular member 172 within the outer tubular member 170. The balloon catheter 150 has an inflatable balloon 160 disposed on the distal end of the outer tubular member 170. The annular space between the outer tubular member 170 and the inner tubular member 172 forms a fluid supply lumen 158 for inflating the balloon 160. The balloon catheter 150 is advanced to a target site within the vascular system of a patient through an introducer sheath. Once in place, treatment catheters may be advanced to the target site through the working lumen 152 of the inner tubular member 172. Accordingly, the prior balloon catheters, such as the balloon catheter 150, required at least three catheter shaft thicknesses (the combined thicknesses of the outer tubular member 170, the inner tubular member 172 and the introducer sheath).

The use of balloon catheters in the neurological vasculature presents a number of catheter design challenges. For one, the blood vessels in the brain are typically very small in diameter, as small as several millimeters or less, requiring that a catheter advanced into these blood vessels have an outside diameter as small as one French (0.33 mm). Furthermore, the brain vasculature is highly tortuous, requiring that a neurological catheter be very flexible, especially at the distal end, to travel through and conform to the tortuous path. Also, the blood vessels of the brain are quite fragile, so a neurological catheter must have a smooth, non-traumatic periphery.

Balloon catheters generally require preparation prior advancing the balloon catheter into the vasculature of a patient by purging any unwanted air bubbles out of the respective balloon inflation lumen and balloon interior. As described above, a balloon catheter typically has an elongated tube and an inflation lumen. In some cases, a balloon catheter may also have multiple tubes (e.g., concentric tubes with an inner tube disposed within an outer tube). Each of these structures, including the tube(s), inflation lumen, and balloon must be purged of air with a fluid (e.g., saline) prior to advancing the balloon catheter through the vasculature of the patient to prevent air from being introduced into the patient which can cause embolisms or other trauma in the patient.

However, due to the closed-end fluid path from the inflation lumen to the balloon, and in many cases, within the working lumen of the balloon catheter, it is difficult and very time-consuming to purge all of the air from system. It is also difficult to determine when all of the air has been purged because of the closed-end fluid paths. As a result, purging the air from prior balloon catheters during preparation for surgery often takes up to 15 minutes, and even then, the purging is not always successful. A typical procedure for purging air from the tube(s) of a prior balloon catheter involves a number of steps. First, a valve such as a luer-activated valve or 3-way stopcock, is attached to the balloon hub of the balloon catheter. Then, a purging syringe filled with balloon inflation media is attached to the valve. The purging syringe is larger than an inflation syringe used to inflate the balloon. For instance, the purging syringe may be a 20 mL syringe while the inflation syringe may be a 5 mL syringe. With the purging syringe pointing downward such that the inflation media fills the distal end of the syringe connected to the valve, the syringe plunger is pulled back to aspirate the balloon inflation lumen and balloon (i.e., a negative pressure is created in the balloon inflation lumen and balloon). The negative pressure is maintained until air bubbles stop forming in the syringe. This can take several minutes or more. The steps of aspirating the balloon inflation lumen and balloon, maintaining negative pressure until air bubbles stop forming in the purging syringe, and releasing the plunger to allow media to be drawing into the balloon lumen and balloon are repeated one or more times to ensure air is purged from the inflation lumen and balloon.

The syringe plunger is then released to allow the inflation media to be drawn into the inflation lumen and balloon. The valve is then closed and the purging syringe is removed from the valve. The inflation syringe filled with inflation media is attached to the valve and is used to inject a maximum volume of recommended balloon inflation media into the inflation lumen to inflate the balloon. The inflation syringe is removed from the valve and the balloon is kept inflated until air bubbles diffuse from the balloon. The balloon is also checked for leakage. When there is no more air in the balloon and no leaks are detected, the purging syringe is attached to the valve again with inflation media filling the distal end of the syringe, and the syringe plunger is retracted to create negative pressure on the inflation lumen to deflate the balloon. The purging syringe is then removed and the balloon catheter is purged of air and prepared for use.

SUMMARY

The disclosed inventions are directed to balloon catheters having an innovative configuration which allows for fast preparation and effective purging of air within the balloon inflation lumen and balloon interior. The balloon catheter is generally used for insertion and positioning of therapeutic devices within a vascular system of a patient, although the disclosed inventive concepts may also be employed in other types of balloon catheters. For instance, although not limited to this application, the disclosed balloon catheters may be particularly useful in imaging, diagnosing and/or treating blockages of a blood vessel, such as coronary occlusion or ischemic strokes.

As explained above, balloon catheters typically require preparation prior to use, including purging air from the system before advancing the catheter into the vasculature of a patient. The balloon catheters of the disclosed inventions are configured to allow effective purging of air from the balloon inflation lumen and balloon in a single aspiration step, allowing a simpler and faster preparation procedure than with existing balloon catheters.

In an exemplary embodiment, a balloon catheter includes an elongated, flexible catheter having an open proximal end, an open distal end, and a working lumen extending therebetween; a balloon member having respective proximal and distal ends secured to, and circumferentially around, an outer surface of a distal portion of the catheter, such that an inner surface of the balloon member and an outer surface of the catheter define an inflatable balloon interior, the catheter having an inflation lumen having a proximal end connected to an inflation port, the inflation lumen extending distally from the inflation port to a distal end opening in fluid communication with the inflatable balloon interior; and one or more purge apertures formed through a wall of the distal portion of the catheter, each of the one or more purge apertures forming a fluid path between the inflatable balloon interior and the working lumen of the catheter. Each of the one or more purge apertures is preferably configured to allow air to pass therethrough and to become clogged by a contrast agent.

Optionally, the one or more purge apertures may include a pair of purge apertures circumferentially spaced approximately 180° apart from each other.

Optionally, the one or more purge apertures are located proximal of the balloon member.

Optionally, the one or more purge apertures are located underlying the balloon member, in which case the balloon catheter includes one or more purge flow passages, each purge flow passage extending longitudinally along an outer surface of the catheter from the distal end opening of the inflation lumen to a corresponding purge aperture. In such embodiments, the one or more purge flow passages may comprise respective grooves formed in the outer surface of the catheter underlying the balloon member. Additionally, or alternatively, the one or more purge flow passages may be provided in the form of respective channels formed between a pair of substantially parallel raised ribs on the outer surface of the catheter underlying the balloon member.

In some embodiments, the balloon catheter may further include one or more purge flow channels, each of the one or more flow channels extending between a respective corresponding purge flow passage and purge aperture. In such embodiments, the one or more flow channels may be configured such that pressure from inflation fluid used to inflate the balloon interior collapses and seals the respective flow channel(s). Additionally, the purge aperture(s) are preferably sized and otherwise configured to allow air to pass therethrough and to become clogged by a contrast agent.

In an exemplary embodiment, the balloon catheter may be formed out of an inner tubular member and an outer tubular member, wherein the inflation lumen comprises an annular space between the inner tubular member and outer tubular member, and (optionally) wherein the proximal end of the balloon member is secured to, and circumferentially around, the outer tubular member, and the distal end of the balloon member is secured to, and circumferentially around, the inner tubular member, and wherein the one or more purge apertures are formed through a wall in the inner tubular member.

In another exemplary embodiment, a balloon catheter includes an elongated, flexible catheter having an open proximal end, an open distal end, and a working lumen extending therebetween. A balloon member having respective proximal and distal ends is secured to, and circumferentially around, an outer surface of a distal portion of the catheter, such that an inner surface of the balloon member and an outer surface of the catheter define an inflatable balloon interior, the catheter having an inflation lumen having a proximal end connected to an inflation port, the inflation lumen extending distally from the inflation port to a distal end opening in fluid communication with the inflatable balloon interior. A pair of purge apertures are formed through a wall of the distal portion of the catheter underlying the balloon member, wherein the purge apertures are circumferentially spaced approximately 180° apart from each other, each purge aperture forming a fluid path between the inflatable balloon interior and the working lumen of the catheter, and wherein the purge apertures are sized and configured to allow air to pass therethrough and to become clogged by a contrast agent. The balloon catheter may further include a pair of purge flow passages, each purge flow passage extending longitudinally along an outer surface of the catheter from the distal end opening of the inflation lumen to a corresponding one of the purge apertures. The one or more purge flow passages may comprise respective grooves formed in the outer surface of the catheter underlying the balloon member. Additionally, or alternatively, the one or more purge flow passages may be provided in the form of respective channels formed between a pair of substantially parallel raised ribs on the outer surface of the catheter underlying the balloon member.

In accordance with another aspect of the disclosed inventions, the above-described balloon catheters may be prepared for use in a medical procedure by: (i) sealing the distal end of the working lumen; (ii) connecting a reservoir of inflation media to the inflation port; (iii) connecting a vacuum source to the proximal end of the working lumen; and injecting inflation media from the reservoir through the respective inflation port and inflation lumen, while simultaneously using the vacuum source to aspirate fluid through the working lumen, such that the vacuum source draws the inflation media through the respective one or more purge apertures to thereby purge air from the balloon interior. Without limitation, sealing the distal end of the working lumen may be accomplished by physically plugging the open distal end of the catheter. While not required, a contrast agent may be used as the inflation media, wherein the contrast agent seals the one or more purge apertures and inflates the balloon interior. The method may further include inspecting the balloon member for leaks. The inflation media may be injected while simultaneously using the vacuum source to aspirate fluid through the working lumen, such that the vacuum source draws the inflation media through the respective one or more purge flow passages and purge apertures to thereby purge air from the balloon interior.

Other aspects and features of embodiments will become apparent from the detailed description in view of the accompanying figures.

BRIEF DESCRIPTION OF THE DRAWINGS

The foregoing, along with other and further embodiments and aspects of the disclosed inventions, with now be described in greater detail in the below detailed description, to be read in view of the accompanying figures, wherein like reference numerals refer to like elements and the description for like elements shall be applicable for all described embodiments wherever relevant.

DETAILED DESCRIPTION

Figure 1:
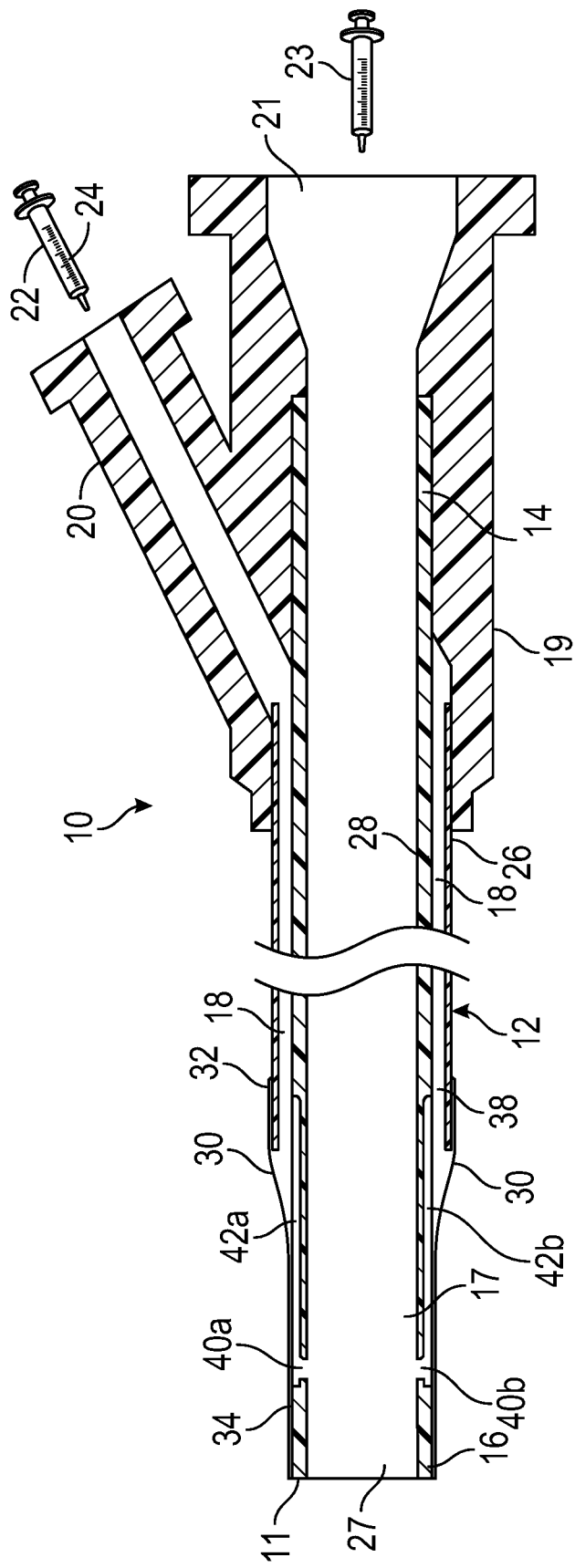
FIG. 1 is a side, partially cut-away cross-sectional view of a balloon guide catheter constructed in accordance with one embodiment of the disclosed inventions.
Figure 2:
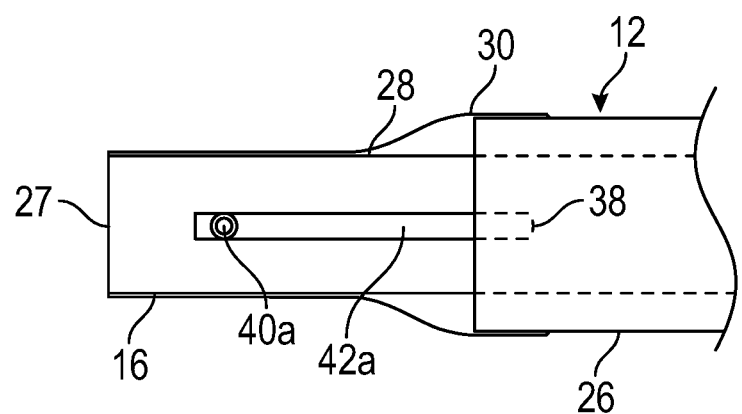
FIG. 2 is a top partially cut-away view of a distal end of the balloon catheter of FIG. 1.

FIGS. 1-5 illustrate a first embodiment of a balloon catheter 10 constructed in accordance with one embodiment of the disclosed inventions. The balloon catheter 10 is configured generally for performing a procedure within a vascular system, such as treating ischemic strokes and/or for blocking or restricting blood flow for other treatment or diagnostic purposes. In particular with respect to the disclosed inventions, the balloon catheter 10 is specially configured to allow for fast preparation for performing a surgical procedure, including providing for fast and effective purging of air from the respective balloon inflation lumen 18 and balloon interior 36 (FIG. 5), as described in greater detail below.

The balloon catheter 10 includes an elongated, flexible, tubular body 12 having a proximal portion 14, a distal portion 16 and an inner working lumen 17 extending therebetween. The working lumen 17 is in fluid communication with a distal opening 27 at a distal end 11 of the tubular body 12, and with a proximal opening 21 defined by a proximal end hub 19 (further described below) secured to the proximal portion 14 of the tubular body 12.

The tubular body 12 includes an outer tubular member 26 and an inner tubular member 28 coaxially disposed within the outer tubular member 26. The respective outer and inner members 26 and 28 may each be made of a polymeric tube, or other suitable material, and may have one or more reinforcing members (not shown) to provide reinforced and/or stiffened portions, as is well-known in the art. For example, a coil, braid, ribbon, hypotube, or other structural member may be disposed on the inside, on the outside, and/or embedded within a wall of one or both of the inner and outer members 28 and 26 along predetermined portion thereof. Such reinforcing members may be made of any suitable material, such as a super-elastic alloy or shape-memory material to provide a specific shape to the reinforced portion of the tubular body 12 under certain conditions.

As mentioned above, the balloon catheter 10 further includes a proximal end hub 19 secured to the proximal portion 14 of the tubular body 12 (i.e., to each of the inner and outer tubular members 28 and 26), wherein the hub 19 defines the proximal end opening 21 of the working lumen 17. The hub 19 includes a balloon inflation port 20 in fluid communication with the proximal end of a balloon inflation lumen 18 that is formed by an annular space between an inner surface of the outer tubular member 26 and an outer surface of the inner tubular member 28. The inflation lumen 18 extends along the length of the tubular body 12 from the balloon inflation part 20 to an inflatable interior 36 (best seen in FIG. 5 in which the balloon interior 36) of a balloon formed by an elastomeric balloon member 30 attached to the distal end portion 16 of the tubular body 12. It should be appreciated that the outer and inner tubular member 26 and 28 may be bonded to each other at one or more locations (not shown) distal of the hub 19. However, such bonds are not fully circumferential so as to ensure the inflation lumen is continuous from the inflation port 20 to the balloon interior. Alternatively, the inflation lumen 18 may be one or more channels, conduits, tubes, etc., formed in, or attached to, the wall of the tubular body 12.

Figure 5:
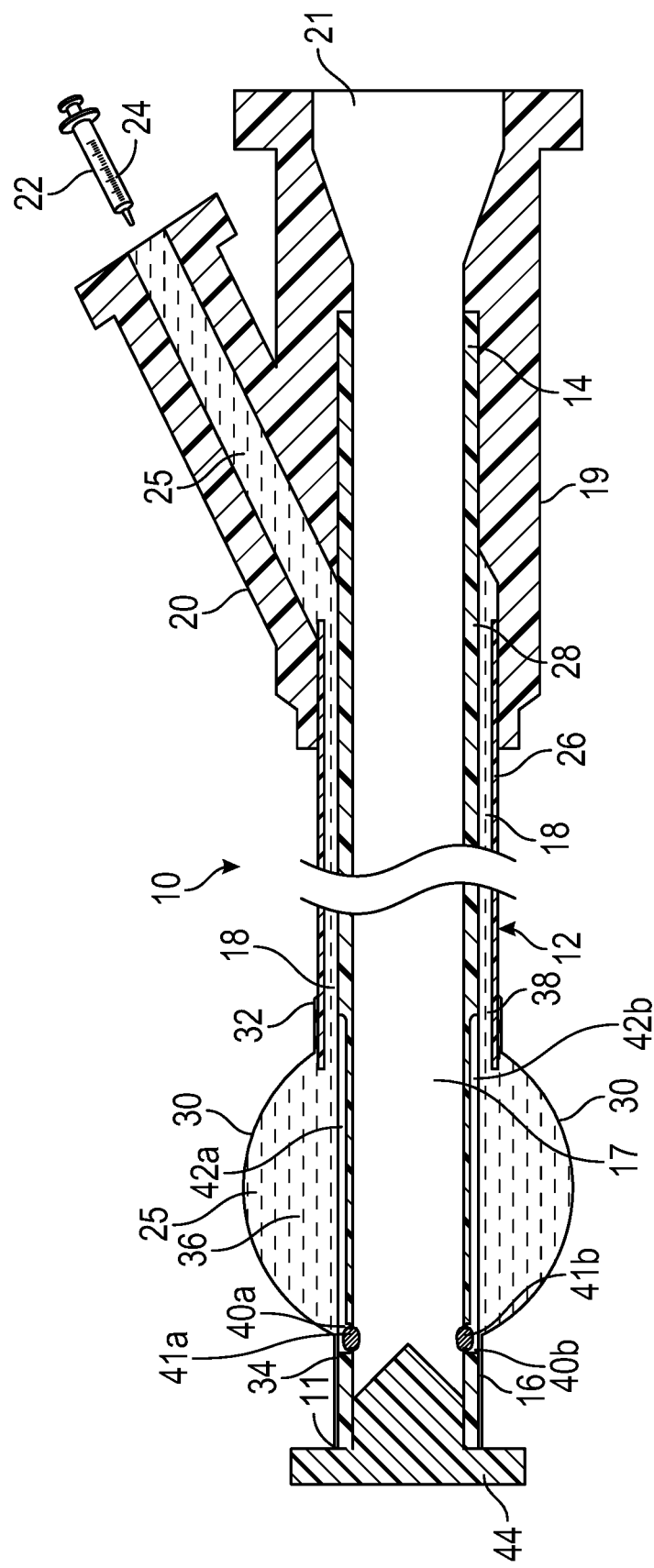
FIG. 5 depicts the balloon catheter as shown in FIG. 4, with the purge aperture sealed and the balloon inflated with inflation media.
Figure 6:
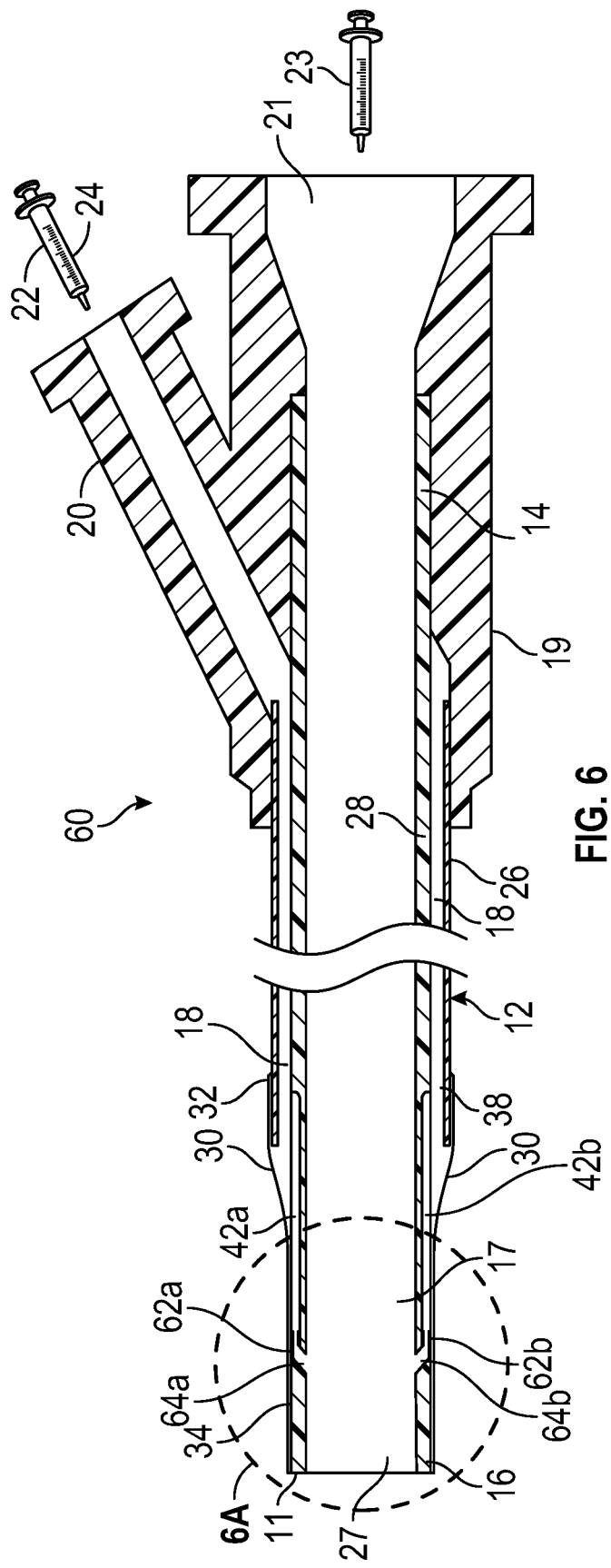
FIG. 6 is a side, partially cut-away cross-sectional view of an alternative balloon catheter constructed in accordance with another embodiment of the disclosed inventions.
Figure 6A:
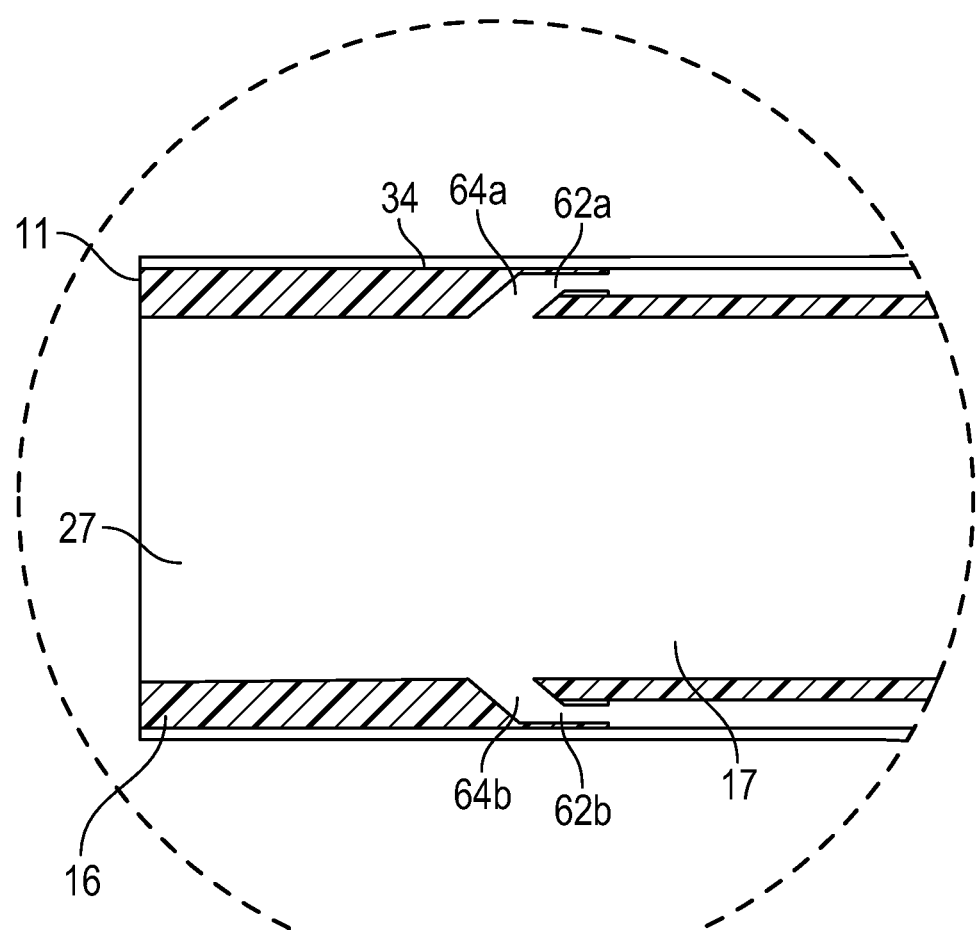
FIG. 6A is an enlarged cross-sectional view of a distal end portion of the balloon catheter of FIG. 6.

In the illustrated embodiment, the balloon member 30 has a proximal portion 32 bonded around a circumference of, so as to form a seal with, an outer surface of a distal end portion of the outer tubular member 26, and a distal end portion 34 bonded around a circumference of, so as to form a seal with, an outer surface of a distal end portion of the inner tubular member 28, such that an inner surface of the balloon member 30 and an outer surface of the inner tubular member 28 (extending beyond the end of the outer tubular member 26) define the inflatable balloon interior 36 (FIG. 5). It should be understood that, in alternate embodiments, the balloon member 30 may be secured at any suitable location on the tubular body 12, such as proximal to the distal portion 16, in the middle portion of the tubular body 12, etc.

The balloon inflation port 20 is configured to be connected to an inflation syringe 22 (not drawn to scale) and/or an inflation (e.g., contrast) media reservoir 24 for prepping the catheter 10 for a surgical procedure. For example, the inflation port 20 may have a female Luer lock (not shown) for attaching the inflation syringe 22, or other fluid source, having a mating male Luer lock. The proximal end opening 21 of the working lumen 17 is configured to be selectively connected to a vacuum source, such as a purging or "aspiration" syringe 23 (not drawn to scale). Towards this end, the hub 19 may have a female Luer lock (not shown) for attaching the aspiration syringe 23, or other aspirating device, having a mating male Luer lock.

A pair of purge apertures 40a and 40b are disposed approximately 180° offset from each other around the circumference of the inner tubular member 28 within the inflatable balloon interior 36. In the illustrated embodiment, each purge aperture 40a, 40b is a small opening formed through the inner tubular member 28 that creates a fluid flow path between the balloon interior 36 and the working lumen 17. A corresponding pair of purge grooves 42a and 42b are formed in the outer surface of the inner tubular member 28 approximately 180° offset from each other around the circumference of the inner tubular member 28, with purge groove 42a extending from the inflation lumen 18 to purge aperture 40a, and purge groove 42b extending from the inflation lumen 18 to purge aperture 40b. As better shown in the top view of the tubular member 12 in FIG. 2, purge groove 42a is a narrow groove formed in the outer surface of the inner tubular member 28 that extends longitudinally (i.e., in the direction of the longitudinal axis of the tubular body 12) from the distal end 38 of the inflation lumen 18 to the purge aperture 40a. While not separately depicted in a top view, purge groove 42b is also a narrow groove formed in the outer surface of the inner tubular member 28 that extends longitudinally from the distal end 38 of the inflation lumen 18 to the purge aperture 40b. The respective purge grooves 42a and 42b function to maintain a fluid flow path between the inflation lumen 18 and the respective purge apertures 40a and 40b underneath the balloon member 30 when the balloon member 30 is collapsed (deflated) onto the outer surface of the inner tubular member 28 (as shown in FIG. 1).

In alternate embodiments, the balloon catheter 10 may have only a single purge aperture and purge groove, or it may have three, four, five, six, or more purge apertures and corresponding purge grooves, which may be evenly (or unevenly) spaced angularly around the circumference of the tubular body 12. In the case of multiple purge apertures and respective purge grooves 42 connecting each to the balloon inflation lumen 18, the structure of each purge aperture 40 and respective purge groove 42 is preferably substantially the same as those shown in the figures and described herein.

A method of preparing the balloon catheter 10 for use in a medical procedure will now be described with reference to FIGS. 3-5. The method is specifically directed to purging air from the balloon catheter 10 and inspecting the balloon catheter 10 for leaks prior to use of the balloon catheter in a surgical procedure. The innovative design of the balloon catheter 10 advantageously allows it to be effectively purged in a single, fast aspiration procedure.

Figure 3:
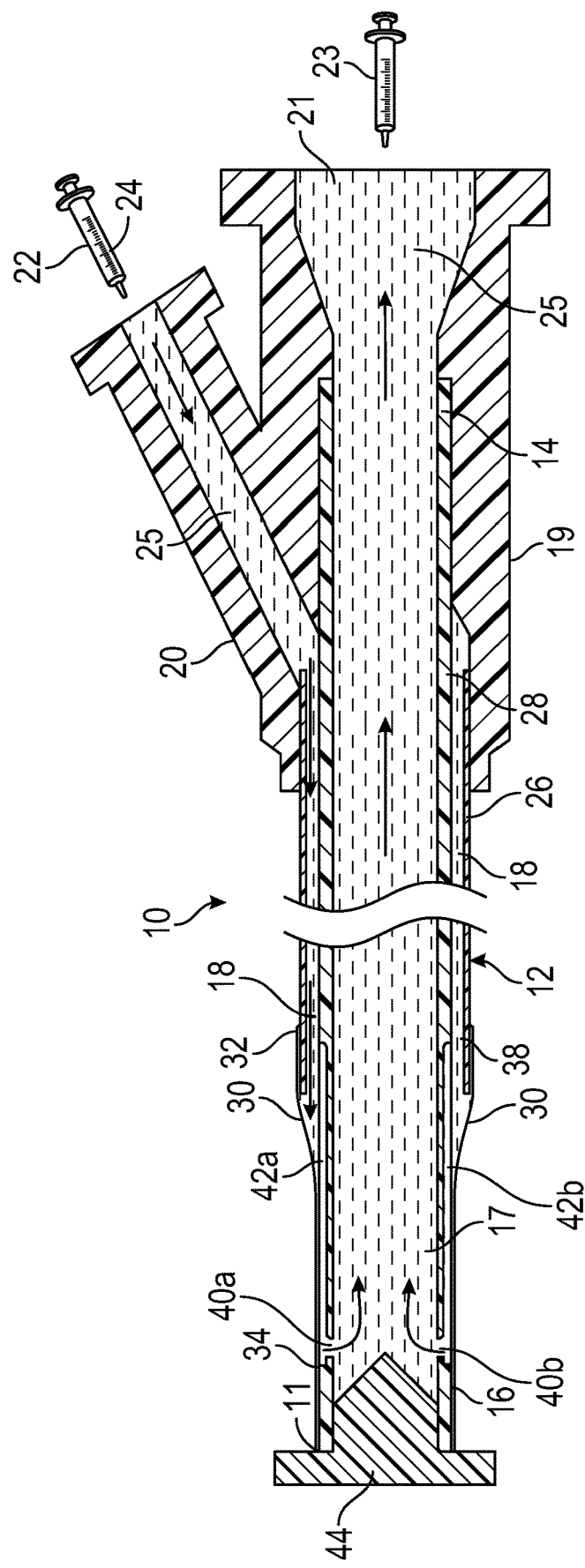
FIG. 3 depicts the balloon catheter of FIG. 1, with the distal end opening plugged and the balloon inflation lumen being purged with inflation media, and wherein the purge aperture initially allows the inflation media and purged air bubbles to pass from the balloon interior into the working lumen of the balloon catheter and aspirated out a proximal end opening thereof.

Referring to FIG. 3, first, the distal end opening 27 of the working lumen 17 is plugged (i.e., corked) with a tip plug 44. Alternatively, the distal end of the working lumen 17 may be plugged using a finger of a user, or other suitable means. A reservoir (e.g., injection syringe) 22 containing an inflation media 25, such as a saline/contrast agent mixture, is fluidly connected to the inflation port 20, and a vacuum source (e.g., purging syringe) 23 is fluidly connected to the proximal opening of the working lumen 17. The inflation media is introduced from the inflation syringe 22 into the respective inflation port 20, inflation lumen 18 and inflatable balloon interior 36. At the same time, the plunger on the purging syringe 23 is pulled back to create a vacuum in the working lumen 17, which draws the inflation fluid 25 from the distal opening of the inflation lumen 38, through the respective purge grooves 42a, 42b and purge apertures 40a and 40b, and into the working lumen 17, thereby purging any air trapped in the respective inflation lumen 18, balloon interior 36 and working lumen 17 of the balloon catheter 10.

Figure 4:
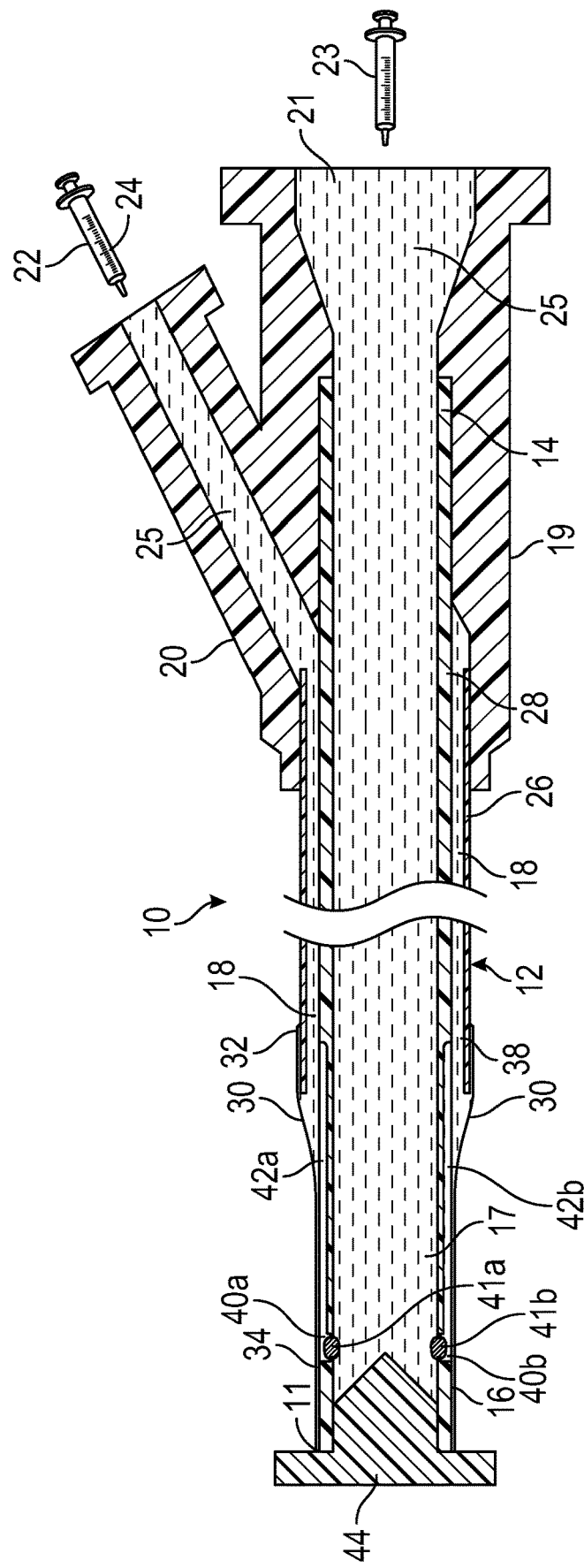
FIG. 4 depicts the balloon catheter as shown FIG. 3, after the purge aperture has been sealed by the inflation media, but with the balloon still deflated.

As shown in FIG. 4, after the interior passages of the balloon catheter have 10 been purged of air by the inflation media 25, but before inflation of the balloon interior 36, particles of the inflation media 25 form clogging matter "plugs" 41a, 41b which seal the respective purge apertures 40a, 40b. Thereby isolating the balloon interior 36 from the working lumen 17. In particular, the purge apertures 40a, 40b have a relatively small diameter that allows air molecules to pass through, but get quickly clogged by the inflation media 25 comprising a contrast agent (e.g., a saline/contrast agent mixture) that coagulates to form the plugs 41a, 41b, thereby sealing the purge apertures 40a, 40b, respectively. For example, the purge apertures 40a, 40b may have a diameter from 0.010 mm to 0.10 mm, or from 0.030 mm to 0.070 mm, or from 0.010 mm to 0.025 mm. The diameter of each purge aperture 40a, 40b and the composition of the inflation media 25 are preferably configured/selected such that the inflation fluid 25 forms the plugs 41a, 41b which seal the purge apertures 40a, 40b, within about 3 minutes, or from 1 to 5 minutes, or from 2 to 4 minutes, or less than 5 minutes, or less than 10 minutes, in various embodiments.

Once the purge apertures 40a, 40b are sealed by the coagulated contrast material plugs 41a, 41b, the purging syringe 23 may then be removed from the proximal opening 21 of the working lumen 17, e.g., by detaching the male Luer lock of the purging syringe 23 from the female Luer lock of the opening 21. In the case that the proximal opening 21 of the working lumen includes a Luer fitting, the Luer fitting automatically seals the opening when the purging syringe 23 is removed. Alternatively, the proximal opening 21 of the working lumen may be sealed, e.g., by inserting a plug (not shown) into the opening 21 to keep the working lumen 17 purged of air.

The preparation method may also include inspecting the inflated balloon member 30 for leaks. Since the purge apertures 40a, 40b are sealed by the plugs 41a, 41b, the pressure from the inflation media 25 injected into the inflation port 20 inflates and expands the balloon member 30. The balloon member 30 can then be checked for leakage visually and/or by detecting for pressure decay. The plunger on the inflation syringe 22 is then retracted to create negative pressure on the inflation port 20 and inflation lumen 18 to deflate the balloon member 30. The inflation syringe 22 may optionally be removed, and the inflation port 20 sealed, to maintain the entire balloon catheter 10 purged of air. If the inflation port utilizes a Luer fitting, the Luer fitting automatically seals the inflation port 20 when the inflation syringe 22 is removed. The balloon catheter 10 is now purged of air, checked for leaks, and prepared for use in a medical procedure.

The method of using the prepped balloon catheter 10 in a medical procedure may include any suitable use of the balloon catheter 10. In one exemplary method, the balloon catheter 10 is advanced through an insertion site of a patient and into the vascular system of the patient, such as a vein or artery. Once the balloon member 30 is positioned at a target location within the vascular system, the balloon member 30 is inflated by attaching an inflation syringe 22 filled with inflation media onto the inflation port 20 (e.g., by attaching a male Luer lock of the inflation syringe 22 to the female Luer lock of the inflation port 20), and injecting inflation media 25 into the inflation lumen 18. Since the purge apertures 40a, 40b remain sealed, the pressurized inflation media 25 from the inflation syringe 22 inflates and expands the balloon member 30 and balloon interior 36.

The method of using the prepped balloon catheter 10 in a medical procedure may include any suitable use of the balloon catheter 10. In one exemplary method, the balloon catheter 10 is advanced through an insertion site of a patient and into the vascular system of the patient, such as a vein or artery. Once the balloon member 30 is positioned at a target location within the vascular system, the balloon member 30 is inflated by attaching an inflation syringe 22 filled with inflation media onto the inflation port 20 (e.g., by attaching a male Luer lock of the inflation syringe 22 to the female Luer lock of the inflation port 20), and injecting inflation media 25 into the inflation lumen 18. Since the purge apertures 40a, 40b remain sealed, the pressurized inflation media 25 from the inflation syringe 22 inflates and expands the balloon member 30 and balloon interior 36.

Figure 12:
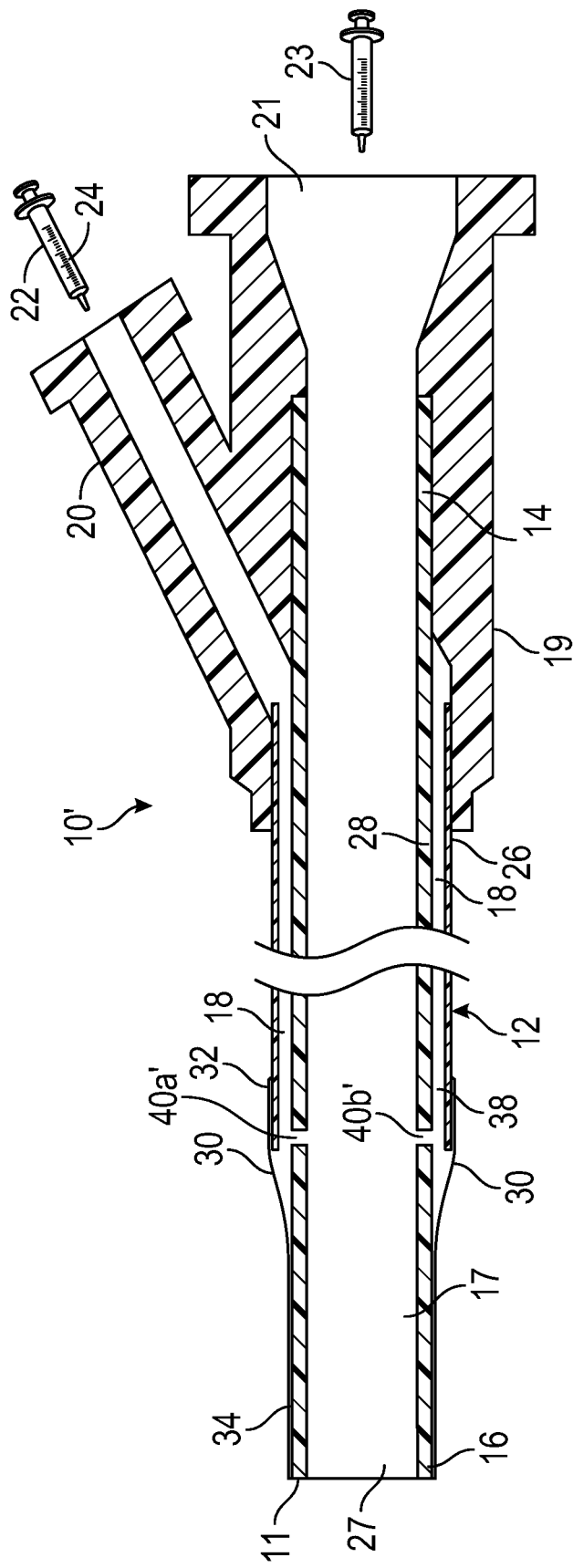
FIG. 12 is a side, partially cut-away cross-sectional view of another alternative balloon catheter constructed in accordance with still further embodiments of the disclosed inventions.
Figure 13A:
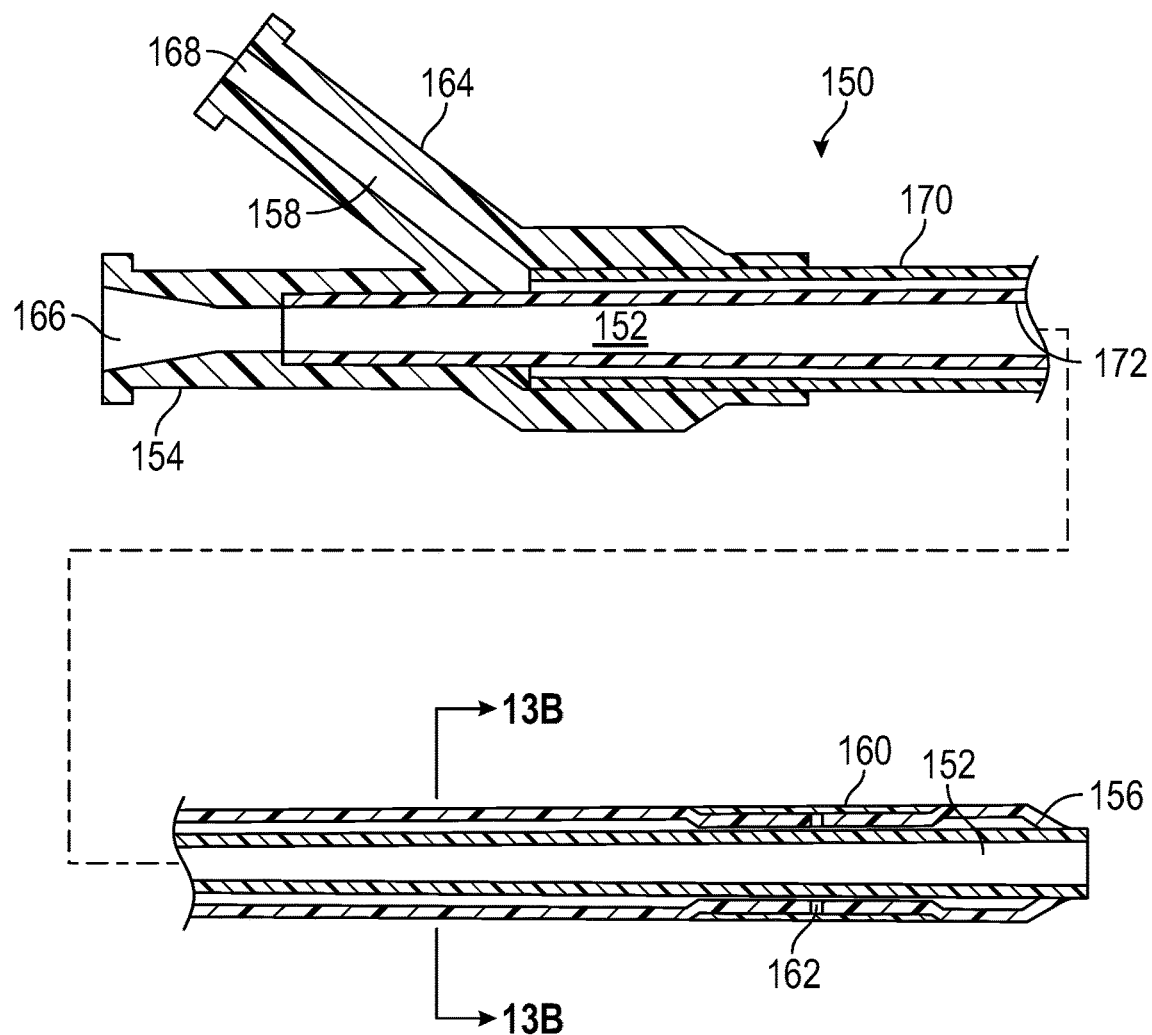
FIGS. 13A and 13B depict a prior art balloon catheter, as disclosed in the U.S. Pat. No. 6,638,245.
Figure 13B:
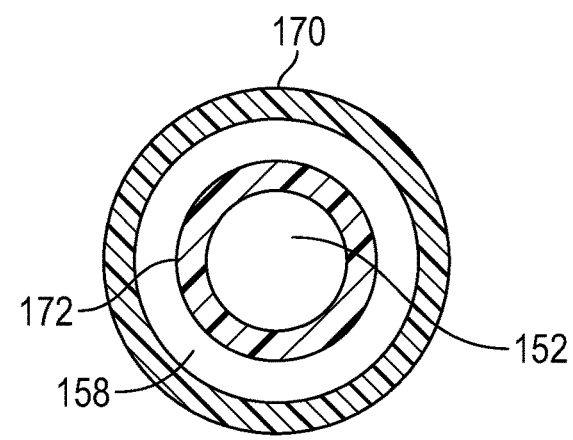

Referring to FIG. 12, an alternate embodiment of the balloon catheter, designated as 10', is constructed substantially the same as the balloon catheter of FIGS. 1-5, except that the purge apertures, designated as 40a' and 40b' are located proximate the distal end 38 of the inflation lumen 18 instead of underlying the balloon member 30. As such, there is no need for the purge grooves 42. Preparation of the alternative balloon catheter 10' is otherwise the same as for balloon catheter 10.

Figure 10:
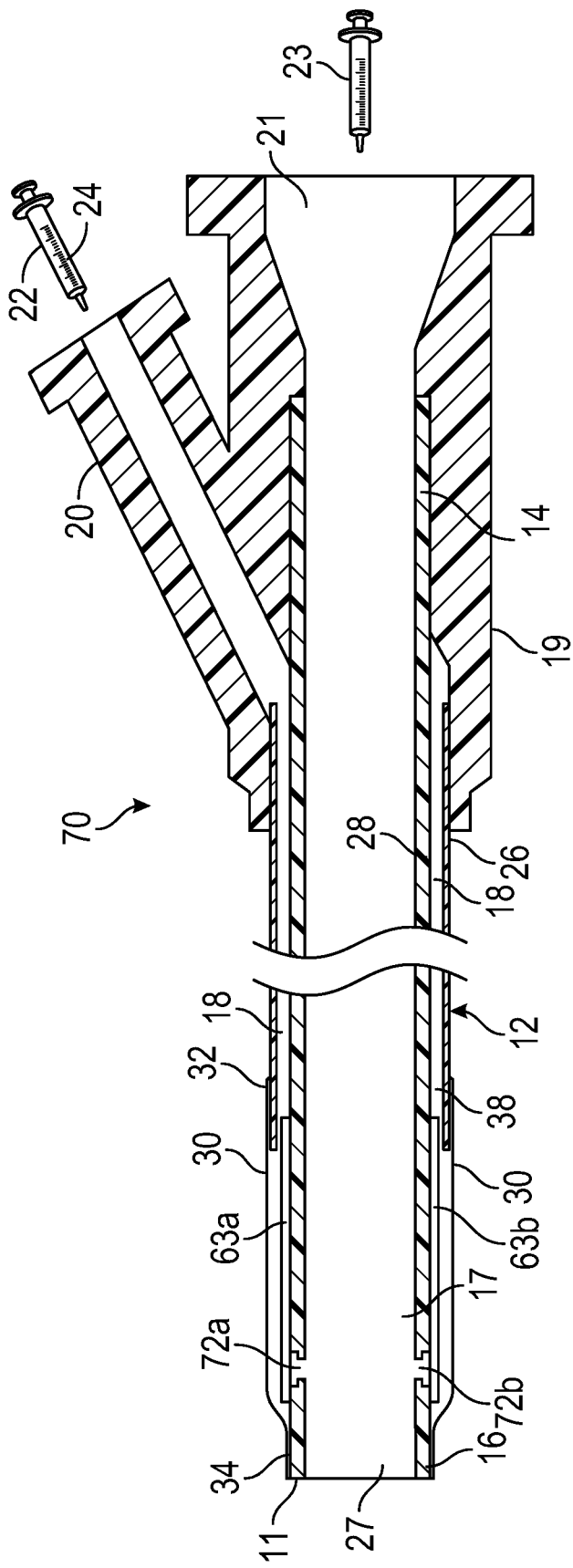
FIG. 10 is a side, partially cut-away cross-sectional view of yet another balloon catheter constructed in accordance with further embodiments of the disclosed inventions.
Figure 11:
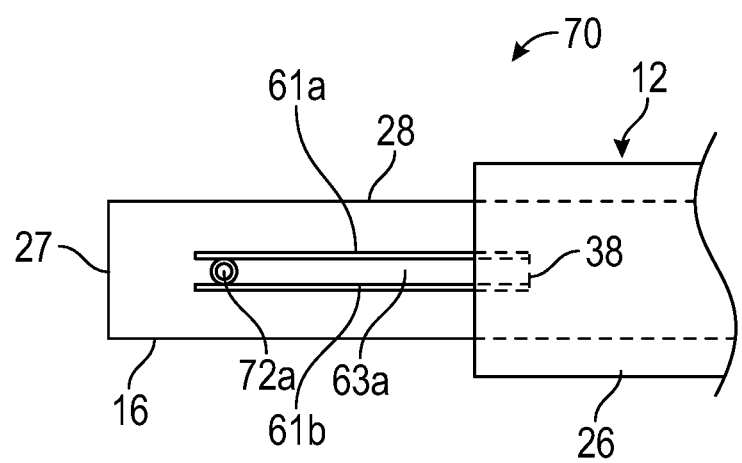
FIG. 11 is a top partially cut-away view of a distal end of the balloon catheter of FIG. 10.

FIGS. 10 and 11 depict yet another alternative embodiment of the balloon catheter 10, designated as 70. The alternative balloon catheter 70 is constructed substantially the same as the balloon catheter 10 of FIGS. 1-5, except that the purge grooves 42a, 42b formed in the outer surface of the inner tubular member 28 are replaced by purge channels 63a, 63b formed by respective parallel raised ribs 61a, 61b (shown for channel 63a in FIG. 11) on the outer surface of the inner tubular member 28, extending from the distal end 38 of the inflation lumen 18 to respective purge apertures 72a and 72b formed through the wall of the inner tubular member 28. Although only channel 63a is shown in detail (FIG. 11), channel 63b is substantially identically formed by a pair of parallel ribs approximately 180° circumferentially offset from channel 63a. In all other aspects, the alternative balloon catheter 70 is the same, and is prepared the same, as balloon catheter 10.

Referring to FIGS. 6-9, another embodiment of a balloon catheter 60 is illustrated. The balloon catheter 60 is substantially the same as the balloon catheter 10, except that instead of purge apertures 40a, 40b, the balloon catheter 60 has respective purge channels 62a, 62b. The purge channels 62a, 62b perform the same function as the purge apertures 40a, 40b in catheter 10. In particular, the purge channels 62a, 62b provide a flow path between the inflatable balloon interior 36 and the working lumen 17 of the tubular body 12. The purge channels 62a, 62b each comprises a fluid channel proximate the distal end 11 of the tubular body 12 within the inflatable balloon interior 36. The purge channels 62a, 62b extend from respective purge apertures 64a, 64b in the wall of the tubular body 12 at the distal end of the purge grooves 42a, 42b to an outlet within the inflatable balloon interior 36. The respective purge channels 62a, 62b may each be formed when punching a hole through the wall of the inner tubular member 28. Like the purge apertures 40a, 40b of catheter 10, the purge channels 62a, 62b are automatically sealed by the inflation media 25 (e.g., a saline/contrast agent mixture) when purging the balloon catheter 60 of air. In addition, while purging the balloon catheter 60 and/or inflating the balloon member 30 during use, the fluid pressure of the inflation media 25 in the balloon interior 36 collapses the respective purge channels 62a, 62b, thereby providing a second, or backup, seal of the purge apertures 64a, 64b.

Figure 14:
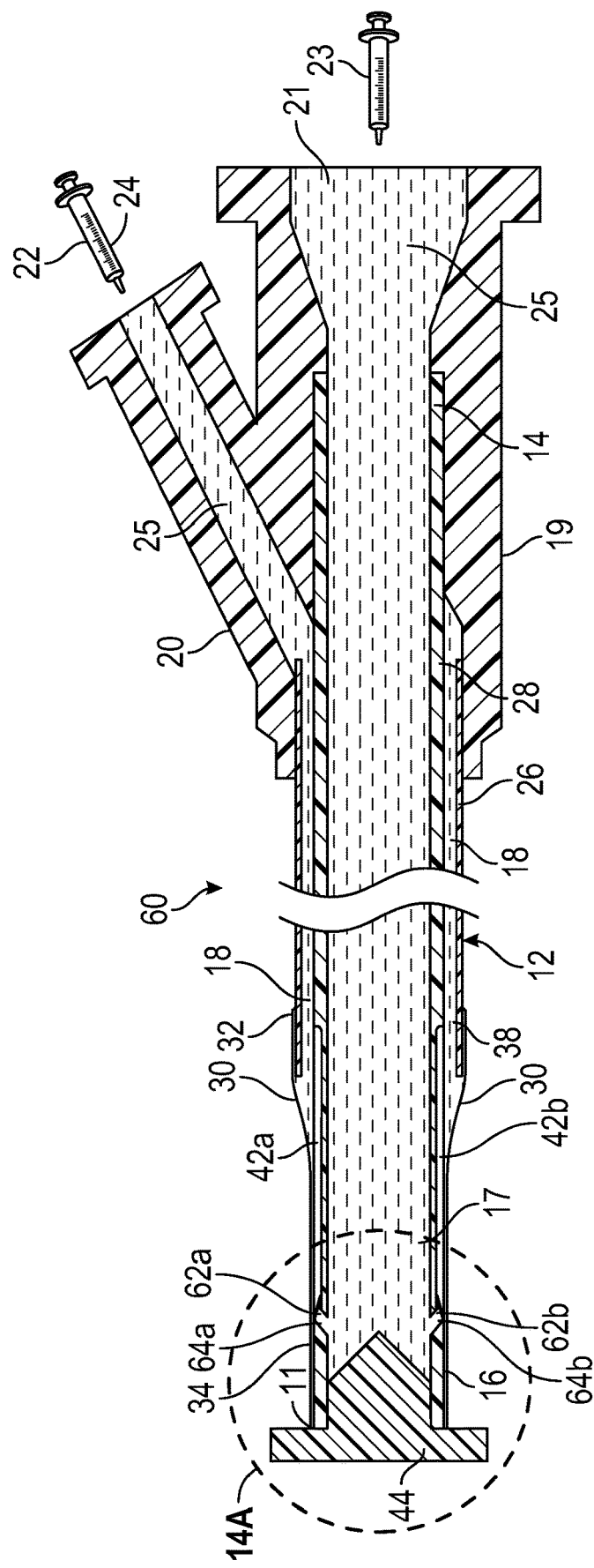
FIG. 14 depicts the balloon catheter as shown FIG. 7, after fluid pressure has collapsed and sealed the purge channel.
Figure 14A:
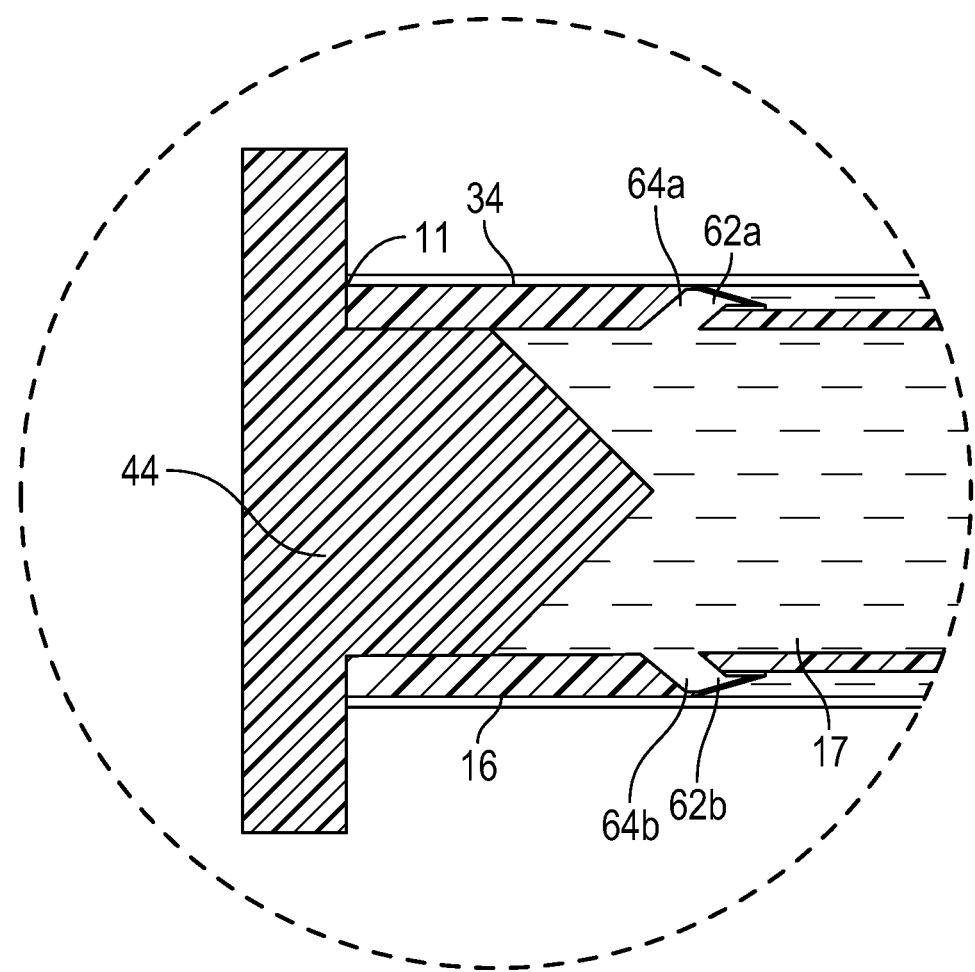
FIG. 14A is an enlarged cross-sectional view of a distal end portion of the balloon catheter of FIG. 14.
Figure 15:
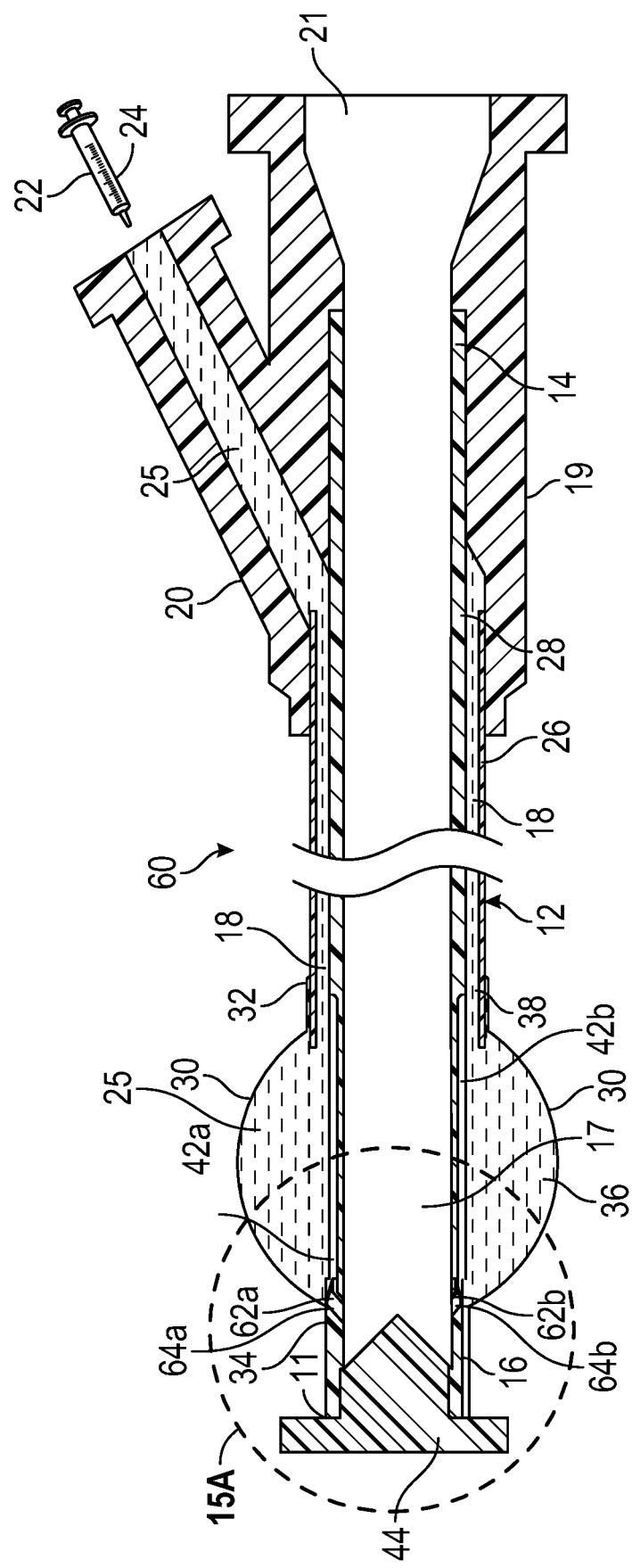
FIG. 15 depicts the balloon catheter as shown in FIG. 14, with the purge channel collapsed and sealed and the balloon inflated with inflation media.
Figure 15A:
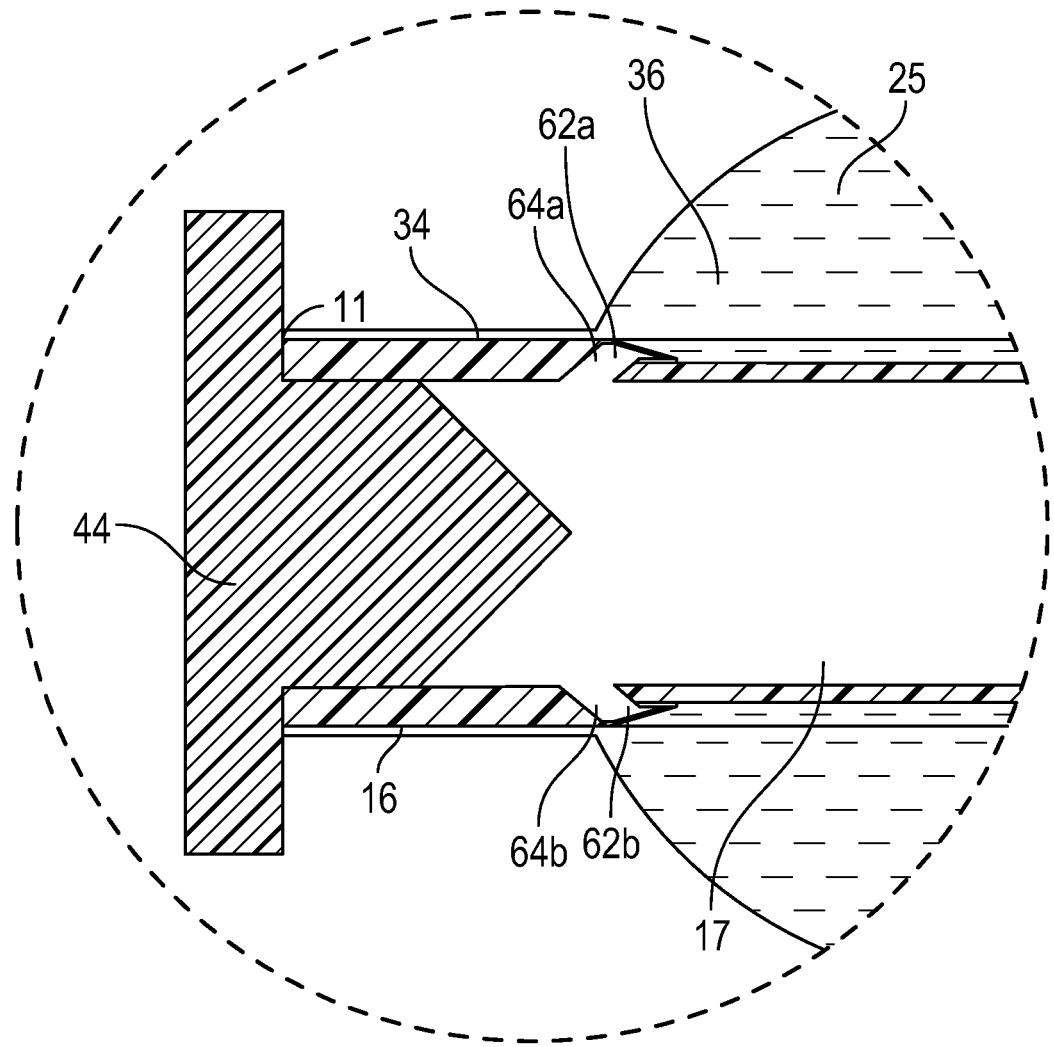
FIG. 15A is an enlarged cross-sectional view of a distal end portion of the balloon catheter of FIG. 15.

As shown in FIGS. 14-15, with the collapsing purge channel feature, the balloon catheter 60 may also be purged and/or used in a medical procedure when injecting an inflation media 25 that does not have particles which form plugs 41a, 41b. Accordingly, the balloon catheter 60 may be purged and/or used in a medical procedure with inflation media 25, such as saline, water, or other suitable media, which does not form clogging matter plugs in the purge channels 62a, 62b. As shown in FIGS. 14-15, the fluid pressure of the inflation media 25 collapses the purge channels 62a, 62b, thereby sealing the purge apertures 64a, 64b.

In alternative embodiments, the balloon catheter 60 may have one or more purge channels 62 and corresponding purge grooves 42. In the illustrated embodiment of FIGS. 6-9 the balloon catheter 60 has two purge channels 62a, 62b fluidly coupled with respective purge grooves 42a, 42b spaced approximately 180° apart on the inner tubular member 28. In other embodiments, the balloon catheter 60 may have three, four, five, six, or more purge apertures 40 and corresponding purge grooves 42, which may be evenly (or unevenly) spaced angularly around the circumference of the inner tubular member 28. In the case of multiple purge channels 62 and purge grooves 42, the structure of each purge channel 62 and purge groove 42 is preferably substantially the same as those shown in the figures and described herein.

The method of preparing the balloon catheter 60 for use in a medical procedure is similar to the above-described method for preparing the balloon catheter 10, preferably including purging air from the balloon catheter 60 and inspecting the balloon member 30 for any leaks. As with the balloon catheter 10, the balloon catheter 60 may also be effectively purged in a single, fast aspiration procedure.

Figure 7:
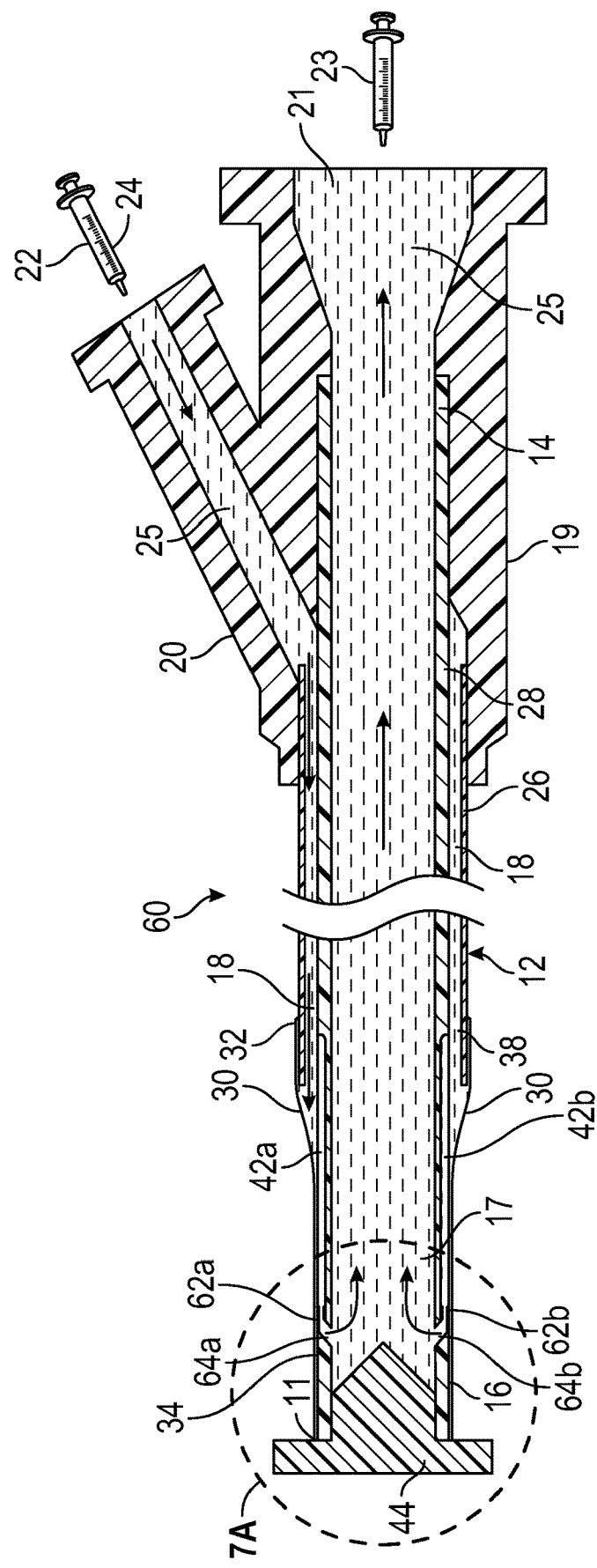
FIG. 7 depicts the balloon catheter of FIG. 6, with the distal end opening plugged and the balloon inflation lumen being purged with inflation media, and wherein the purge aperture initially allows the inflation media and purged air bubbles to pass from the balloon interior into the working lumen of the balloon catheter and aspirated out a proximal end opening thereof.
Figure 7A:
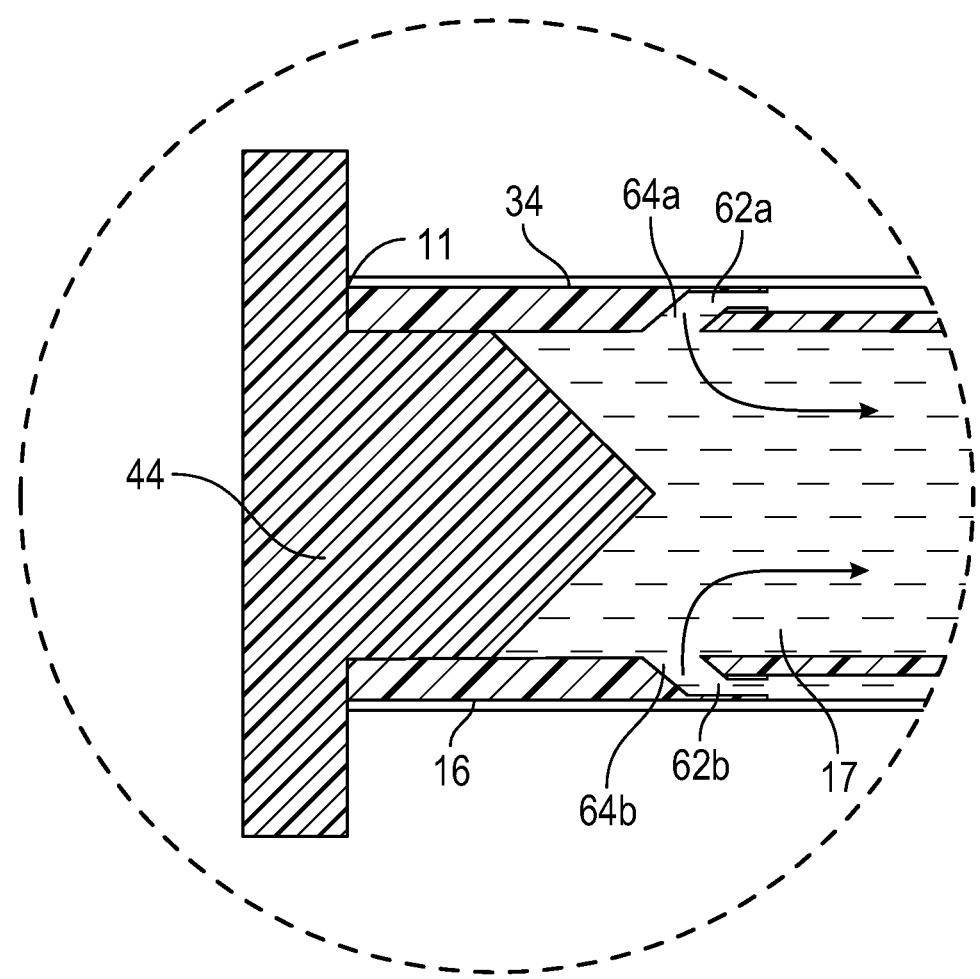
FIG. 7A is an enlarged cross-sectional view of a distal end portion of the balloon catheter of FIG. 7.

Referring to FIG. 7, first, the distal opening 27 of the working lumen 17 is plugged using a tip plug 44. Alternatively, the distal end of the working lumen 17 may be plugged using a finger of a user, or other suitable means. A reservoir 22 of inflation media 25 (such as an inflation syringe 22 filled with a saline/contrast agent mixture) is attached to the inflation port 20. If Luer locks are used, a male Luer lock of the reservoir 22 is attached to the female Luer lock of the inflation port 20. In the embodiment of FIG. 7, a syringe 22 filled with inflation media 25 is attached to the inflation port 20. Then, a vacuum source (e.g., purging syringe) 23 is attached to the proximal opening 21 of the working lumen 17. With Luer locks, a male Luer lock of the vacuum source 23 is attached to the female Luer lock of the proximal lumen opening 21. The inflation media is introduced from the inflation syringe 22 into the respective inflation port 20, inflation lumen 18 and inflatable balloon interior 36. At the same time, the plunger on the purging syringe 23 is pulled back to create a vacuum in the working lumen 17, which draws the inflation fluid 25 from the distal opening of the inflation lumen 38, through the respective purge grooves 42a, 42b, purge channels 62a and 62b, and into the working lumen 17 via purge apertures 64a, 64b, thereby purging any air trapped in the respective inflation lumen 18, balloon interior 36 and working lumen 17 of the balloon catheter 60.

Figure 8:
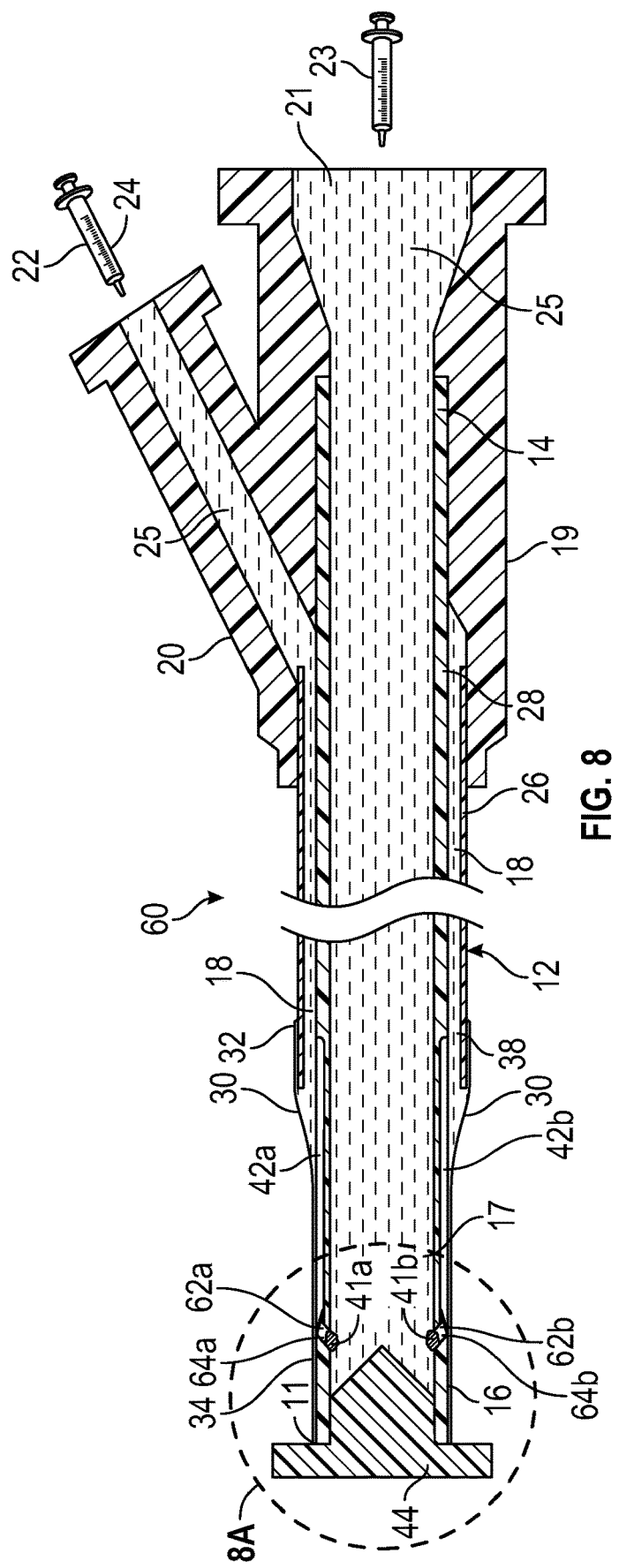
FIG. 8 depicts the balloon catheter as shown FIG. 7, after the purge aperture has been sealed by the inflation media, but with the balloon still deflated.
Figure 8A:
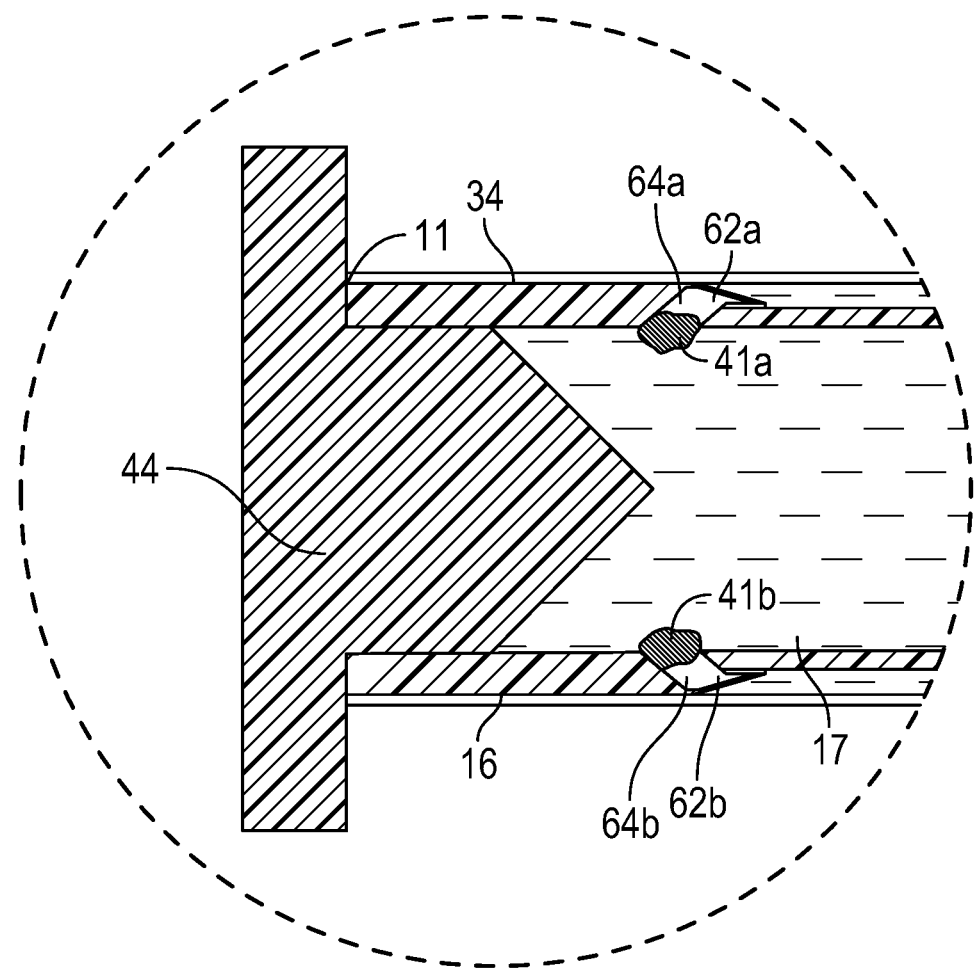
FIG. 8A is an enlarged cross-sectional view of a distal end portion of the balloon catheter of FIG. 8.

As shown in FIG. 8, after the balloon catheter 60 has been purged with inflation media 25, the coagulated inflation media 25 forms respective plugs 41a, 41b that seal the purge channels/apertures 62a, 62b and 64a, 64b. In particular, the purge channels 62a, 62b have a small diameter such that the inflation media 25 comprising a contrast agent (e.g., a saline/contrast agent mixture) will form the plugs 41a, 41b, thereby sealing the purge channels/apertures 62a, 62b and 64a, 64b within a certain sealing time from when the inflation media 25 is introduced. For example, the purge channels 62a, 62b may have a diameter from 0.010 mm to 0.10 mm, or from 0.030 mm to 0.070 mm, or from 0.010 mm to 0.025 mm. The diameter of the purge channels 62a, 62b and composition of the inflation media 25 may be configured/selected such that the inflation fluid 25 forms the sealing plugs 41a, 41b within about 3 minutes, or from 1 to 5 minutes, or from 2 to 4 minutes, or less than 5 minutes or less than 10 minutes. The purge channels 62a, 62b may also be sealed when the fluid pressure of the inflation media 25 (e.g., the fluid pressure of the inflation media 25 in the balloon interior 36) collapses the respective purge channels 62a, 62b and seals the purge channels 62a, 62b.

Figure 9:
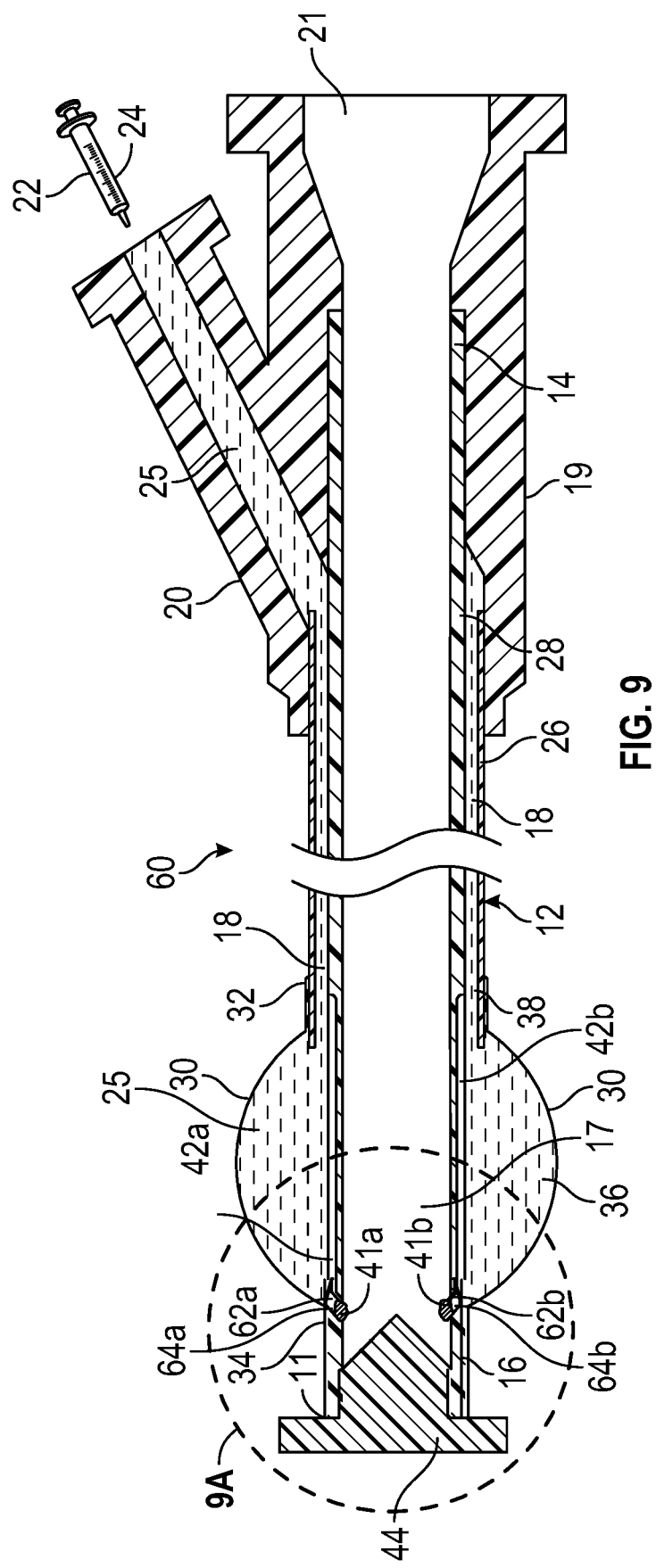
FIG. 9 depicts the balloon catheter as shown in FIG. 8, with the purge aperture sealed and the balloon inflated with inflation media.
Figure 9A:
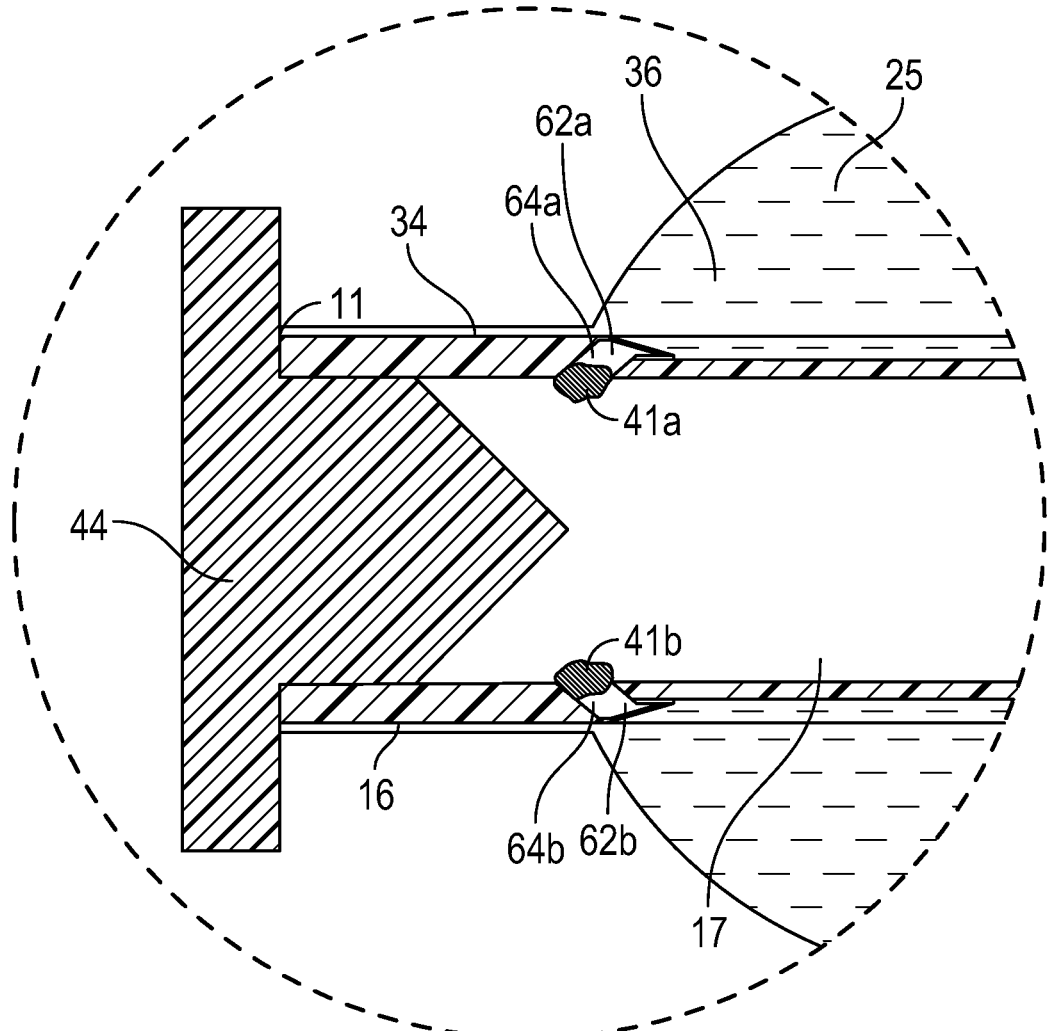
FIG. 9A is an enlarged cross-sectional view of a distal end portion of the balloon catheter of FIG. 9.

With reference to FIGS. 9 and 9A, once the purge channels/apertures 62a, 62b and 64a, 64b are sealed by the contrast material plugs 41a, 41b, the purging syringe 23 may then be removed from the proximal end opening 21 of the working lumen 17, e.g., by detaching the male Luer lock of the purging syringe 23 from the female Luer lock of the opening 21. In the case that the proximal opening 21 of the working lumen includes a Luer fitting, the Luer fitting automatically seals the opening when the purging syringe 23 is removed. Alternatively, the proximal opening 21 of the working lumen may be sealed, e.g., by inserting a plug (not shown) into the opening 21 to keep the working lumen 17 purged of air.

As with the balloon catheter 10, the preparation of the balloon catheter 60 preferably also includes inspecting the inflated balloon member 30 for leaks. Since the purge channels/apertures 62a, 62b and 64a, 64b are sealed by the contrast material plugs 41a, 41b, the pressure from the inflation media 25 injected into the inflation port 20 inflates and expands the balloon member 30. The balloon member 30 can then be checked for leakage visually and/or by detecting for pressure decay. The plunger on the inflation syringe 22 is then retracted to create negative pressure on the inflation port 20 and inflation lumen 18 to deflate the balloon member 30. The inflation syringe 22 may optionally be removed, and the inflation port 20 sealed, to maintain the entire balloon catheter 60 purged of air. If the inflation port utilizes a Luer fitting, the Luer fitting automatically seals the inflation port 20 when the inflation syringe 22 is removed. The balloon catheter 60 is now purged of air, checked for leaks, and prepared for use in a medical procedure.

The method of using the prepped balloon catheter 60 in a medical procedure may include any suitable use of the balloon catheter. In one exemplary method, the balloon catheter 60 is advanced through an insertion site of a patient and into the vascular system of the patient, such as a vein or artery. Once the balloon member 30 is positioned at a target location within the vascular system, the balloon member 30 is inflated by attaching an inflation syringe 22 filled with inflation media onto the inflation port 20 (e.g., by attaching a male Luer lock of the inflation syringe 22 to the female Luer lock of the inflation port), and injecting inflation media 25 into the inflation lumen 18. Since the purge channels/apertures 62a, 62b and 64a, 64b remain sealed, the pressurized inflation media 25 from the inflation syringe 22 inflates and expands the balloon member 30. In addition, the inflation pressure also collapses the purge channels 62a, 62b, providing a backup seal.

The method of preparing the balloon catheter 60 for use in a medical procedure and/or using the balloon catheter 60 with an inflation media 25 that does not form plugs (e.g., saline or water) is the same as described above, except that the inflation media 25 does not form the plugs 41a, 41b. Instead, as shown in FIGS. 14-15, the purge channels/apertures 62a, 62b and 64a,64b are sealed when the fluid pressure of the inflation media 25 collapses the respective purge channels 62a, 62b.

Although particular embodiments have been shown and described, it is to be understood that the above description is not intended to limit the scope of these embodiments. While embodiments and variations of the many aspects of the invention have been disclosed and described herein, such disclosure is provided for purposes of explanation and illustration only. Thus, various changes and modifications may be made without departing from the scope of the claims. For example, not all of the components described in the embodiments are necessary, and the invention may include any suitable combinations of the described components, and the general shapes and relative sizes of the components of the invention may be modified. Accordingly, embodiments are intended to exemplify alternatives, modifications, and equivalents that may fall within the scope of the claims. The invention, therefore, should not be limited, except to the following claims, and their equivalents.

What is claimed is:

1. A balloon catheter comprising:
an elongated, flexible catheter having an open proximal end, an open distal end, and a working lumen extending therebetween;
a balloon member having respective proximal and distal ends secured to, and circumferentially around, an outer surface of a distal portion of the catheter, such that an inner surface of the balloon member and an outer surface of the catheter define an inflatable balloon interior, the catheter having an inflation lumen having a proximal end connected to an inflation port, the inflation lumen extending distally from the inflation port to a distal end opening in fluid communication with the inflatable balloon interior; and one or more purge apertures formed through a wall of the distal portion of the catheter, each of the one or more purge apertures forming a fluid path between the inflatable balloon interior and the working lumen of the catheter; and one or more purge flow passages, each purge flow passage extending longitudinally along the outer surface of the catheter from the distal end opening of the inflation lumen to a corresponding purge aperture.

2. The balloon catheter of claim 1, wherein each of the one or more purge apertures is configured to allow air to pass therethrough and to become clogged by a contrast agent.

3. The balloon catheter of claim 1, wherein the one or more purge apertures comprise a pair of purge apertures circumferentially spaced approximately 180° apart from each other.

4. The balloon catheter of claim 3, wherein each of the one or more purge apertures is configured to allow air to pass therethrough and to become clogged by a contrast agent.

5. The balloon catheter of claim 1, wherein the one or more purge apertures are located underlying the balloon member.

6. The balloon catheter of claim 5, wherein each of the one or more purge apertures is configured to allow air to pass therethrough and to become clogged by a contrast agent.

7. The balloon catheter of claim 1, wherein each of the one or more purge flow passages comprises a pair of substantially parallel raised ribs on the outer surface of the catheter underlying the balloon member.

8. The balloon catheter of claim 1, wherein the catheter comprises an inner tubular member and an outer tubular member, and wherein the inflation lumen comprises an annular space between the inner tubular member and outer tubular member.

9. The balloon catheter of claim 8, wherein the proximal end of the balloon member is secured to, and circumferentially around, the outer tubular member, and the distal end of the balloon member is secured to, and circumferentially around, the inner tubular member, and wherein each of the one or more purge apertures is formed through a wall in the inner tubular member.

10. The balloon catheter of claim 1, wherein each of the one or more purge flow passages comprises a groove formed in the outer surface of the catheter underlying the balloon member.

11. A method of preparing the balloon catheter of claim 10 for use in a medical procedure, the method comprising:
sealing the distal end of the working lumen;
connecting a reservoir of inflation media to the inflation port;
connecting a vacuum source to the proximal end of the working lumen; and
injecting inflation media from the reservoir through the inflation port and inflation lumen, while simultaneously using the vacuum source to aspirate fluid through the working lumen, such that the vacuum source draws the inflation media through the one or more purge flow passages and purge apertures to thereby purge air from the balloon interior.

12. The method of claim 11, wherein sealing the distal end of the working lumen comprises physically plugging the open distal end of the catheter.

13. The method of claim 11, wherein the inflation media seals the one or more purge apertures and inflates the balloon interior, the method further comprising inspecting the balloon member for leaks.

14. The balloon catheter of claim 1, wherein each of the one or more purge flow passages comprises a purge flow channel extending between a respective corresponding purge flow passage and purge aperture.

15. The balloon catheter of claim 14, wherein each of the one or more purge flow channels is configured such that pressure from inflation fluid used to inflate the balloon interior collapses and seals the flow channel.

16. The balloon catheter of claim 14, wherein each of the one or more purge apertures is configured to allow air to pass therethrough and to become clogged by a contrast agent.

17. A method of preparing the balloon catheter of claim 14 for use in a medical procedure, the method comprising:
sealing the distal end of the working lumen;
connecting a reservoir of inflation media to the inflation port;
connecting a vacuum source to the proximal end of the working lumen; and
injecting inflation media from the reservoir through the inflation port and inflation lumen, while simultaneously using the vacuum source to aspirate fluid through the working lumen, such that the vacuum source draws the inflation media through the one or more purge flow passages, purge flow channels and purge apertures, to thereby purge air from the balloon interior.

18. The method of claim 17, wherein each of the one or more purge flow channels is configured such that pressure from inflation fluid used to inflate the balloon interior collapses and seals the flow channel.

19. A method of preparing the balloon catheter of claim 1 for use in a medical procedure, the method comprising:
sealing the distal end of the working lumen;
connecting a reservoir of inflation media to the inflation port;
connecting a vacuum source to the proximal end of the working lumen; and
injecting inflation media from the reservoir through the inflation port and inflation lumen, while simultaneously using the vacuum source to aspirate fluid through the working lumen, such that the vacuum source draws the inflation media through the one or more purge apertures to thereby purge air from the balloon interior.

20. The method of claim 19, wherein sealing the distal end of the working lumen comprises physically plugging the open distal end of the catheter.

21. The method of claim 19, wherein the inflation media seals the one or more purge apertures and inflates the balloon interior, the method further comprising inspecting the balloon member for leaks.

22. A balloon catheter comprising:
an elongated, flexible catheter having an open proximal end, an open distal end, and a working lumen extending therebetween;
a balloon member having respective proximal and distal ends secured to, and circumferentially around, an outer surface of a distal portion of the catheter, such that an inner surface of the balloon member and an outer surface of the catheter define an inflatable balloon interior, the catheter having an inflation lumen having a proximal end connected to an inflation port, the inflation lumen extending distally from the inflation port to a distal end opening in fluid communication with the inflatable balloon interior;

a pair of purge apertures formed through a wall of the distal portion of the catheter underlying the balloon member, wherein the purge apertures are circumferentially spaced approximately 180° apart from each other, each purge aperture forming a fluid path between the inflatable balloon interior and the working lumen of the catheter, and wherein the purge apertures are sized and configured to allow air to pass therethrough and to become clogged by a contrast agent; and a pair of purge flow passages, each purge flow passage extending longitudinally along the outer surface of the catheter from the distal end opening of the inflation lumen to a corresponding one of the purge apertures.

23. The balloon catheter of claim 22, wherein each of the one or more purge flow passages comprises a groove formed in the outer surface of the catheter underlying the balloon member.

24. The balloon catheter of claim 22, wherein each of the one or more purge flow passages comprises a channel formed between a pair of substantially parallel raised ribs on the outer surface of the catheter underlying the balloon member.

\* \* \* \* \*